(12) United States Patent
Verbeek

(10) Patent No.: US 8,986,317 B2
(45) Date of Patent: Mar. 24, 2015

(54) INSTRUMENT AND METHOD FOR MAKING THE SAME

(75) Inventor: Marcel Antonius Elisabeth Verbeek, Heerlen (NL)

(73) Assignee: Fortimedix Surgical B.V., Nuth (NL)

( * ) Notice: Subject to any disclaimer, the term of this patent is extended or adjusted under 35 U.S.C. 154(b) by 17 days.

(21) Appl. No.: 12/921,475

(22) PCT Filed: Jun. 30, 2008

(86) PCT No.: PCT/EP2008/005319
§ 371 (c)(1),
(2), (4) Date: Oct. 19, 2010

(87) PCT Pub. No.: WO2009/112060
PCT Pub. Date: Sep. 17, 2009

(65) Prior Publication Data
US 2011/0034764 A1 Feb. 10, 2011

(30) Foreign Application Priority Data

Mar. 10, 2008 (EP) .................................. 08004373

(51) Int. Cl.
*A61B 1/00* (2006.01)
*B23K 26/00* (2014.01)
(Continued)

(52) U.S. Cl.
CPC ............ *A61B 1/0055* (2013.01); *A61B 1/00071* (2013.01); *A61B 1/0011* (2013.01); *A61M 25/0013* (2013.01); *A61M 25/0138* (2013.01);
(Continued)

(58) Field of Classification Search
CPC .............. A61M 2025/09066; A61M 25/0051; A61M 25/0053; A61M 25/0013; A61M 25/0138; A61M 25/001; A61M 25/0054; C23F 1/02; F16D 3/50; A61F 2/90; A61B 1/0055; A61B 1/00071; A61B 1/0011; A61B 1/00073
See application file for complete search history.

(56) References Cited

U.S. PATENT DOCUMENTS 6,086,773 A 7/2000 Dufresne et al.
6,107,004 A * 8/2000 Donadio, III ................. 430/320
(Continued)

FOREIGN PATENT DOCUMENTS

DE 10 2007 019 779 10/2007
EP 0 916 359 5/1999
(Continued)

OTHER PUBLICATIONS

International Search Report issued Nov. 18, 2008 in International (PCT) Application No. PCT/EP2008/005319.

*Primary Examiner* — Gary Jackson
*Assistant Examiner* — Scott T. Luan
(74) *Attorney, Agent, or Firm* — Wenderoth, Lind & Ponack, L.L.P.

(57) ABSTRACT

A process for producing the actuating part of an instrument for endoscopic applications, which instrument comprises a tubular member having a handling end portion with a flexible portion and an actuating device located at another end portion, which actuating device comprises a cylindrical part connected to the handling end portion, a cylindrical part connected to the actuating device and a number of longitudinal elements for transferring the movement of the actuating device to the handling end portion, the actuating device being made beginning with a full cylindrical tube which is provided with a number of longitudinal slits thereby forming the longitudinal elements.

32 Claims, 6 Drawing Sheets

(51) Int. Cl.
  *A61B 1/005*  (2006.01)
  *A61M 25/00* (2006.01)
  *A61M 25/01* (2006.01)
(52) U.S. Cl.
  CPC .......... *A61B 1/00073* (2013.01); *A61M 25/001* (2013.01); *A61M 25/0054* (2013.01)
  USPC ..................................... 606/101; 219/121.72

(56) References Cited

U.S. PATENT DOCUMENTS

| | | | |
|---|---|---|---|
| 6,485,411 | B1 | 11/2002 | Konstorum et al. |
| 6,537,459 | B1 | 3/2003 | Dufresne et al. |
| 7,018,330 | B2 | 3/2006 | Alekseenko et al. |
| 2003/0069522 | A1* | 4/2003 | Jacobsen et al. ............ 600/585 |
| 2005/0027287 | A1* | 2/2005 | O'Connor et al. .............. 606/15 |
| 2006/0281566 | A1* | 12/2006 | Lee ............................... 464/149 |
| 2007/0049800 | A1 | 3/2007 | Boulais |
| 2007/0255105 | A1 | 11/2007 | Ochi et al. |
| 2008/0234545 | A1 | 9/2008 | Breedveld et al. |
| 2009/0069632 | A1 | 3/2009 | McIntyre et al. |
| 2011/0004157 | A1 | 1/2011 | Dewaele et al. |

FOREIGN PATENT DOCUMENTS

| | | |
|---|---|---|
| EP | 1 708 609 | 10/2006 |
| JP | 5-20702 | 3/1993 |
| JP | 11-239617 | 9/1999 |
| JP | 2007-516042 | 6/2007 |
| WO | 97/42910 | 11/1997 |
| WO | 99/61261 | 12/1999 |
| WO | 2005/065555 | 7/2005 |
| WO | 2005/067785 | 7/2005 |

* cited by examiner

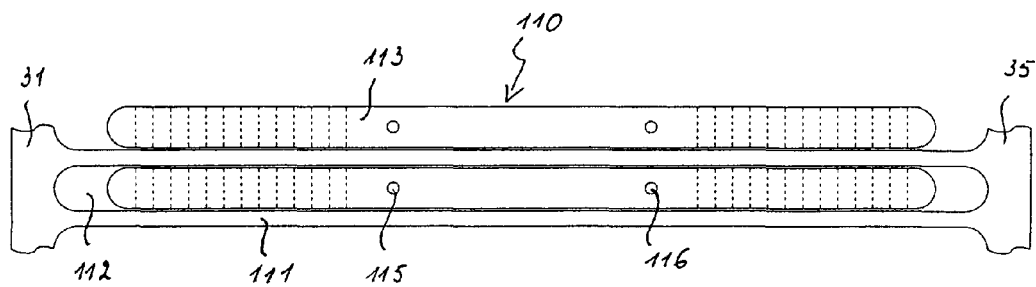
Fig. 9
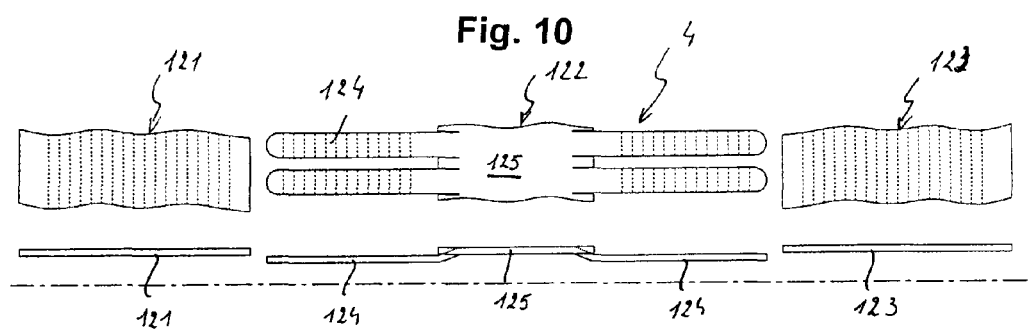
Fig. 10
Fig. 11
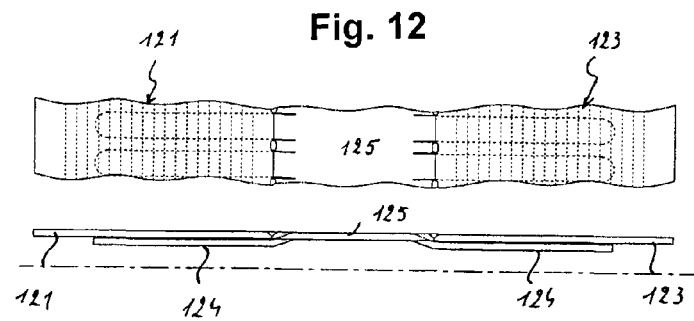
Fig. 12
Fig. 13

US 8,986,317 B2

INSTRUMENT AND METHOD FOR MAKING THE SAME

BACKGROUND OF THE INVENTION

I. Technical Field

The invention relates to a process for producing the actuating part of an instrument for endoscopic applications or the like, which instrument comprises a tubular member having a handling end portion with a flexible portion and an actuating means located at another end portion, which actuating means comprises a cylindrical part connected to the handling end portion, a cylindrical part connected to the actuating means and a number of longitudinal elements for transferring the movement of the actuating means to the handling end portion.

II. Description of the Related Art

An instrument of the above described type has been described in EP-A-1 708 609 and is normally used for applications such as minimally invasive surgery, but it is also applicable for other purposes such as the inspection or repair of mechanical or electronic installations at locations which are difficult to reach. In the detailed description, the term endoscopic applications or endoscopic instrument will be used but the term must be interpreted as also covering other applications or instruments as explained above.

In this known instrument, the actuating part needed to steer one end of the instrument by movement of the other end is made out of a number of cables which are connected both to the first and second end portions. Connecting the cables to these portions is cumbersome and complicated in that each cable has to be connected separately and the tension in the cables must be the same for all of the cables so to obtain a reliable control of the movement. This makes the production of such an instrument complicated.

SUMMARY OF THE INVENTION

It is therefore an object of the invention to provide a process for producing the actuating part of an instrument of the above identified type in which this problem is avoided.

This object is achieved in that the actuating means is made beginning with a full cylindrical tube which is provided with a number of longitudinal slits thereby forming the longitudinal elements.

By having the longitudinal elements made as an integral part of the remaining parts of the actuating operating member, the separate connection of the different parts of this member is avoided and assembling becomes extremely easy.

The invention also relates to an endoscopic instrument using an actuating means obtained by the process according to the invention, in which different constructions are used in order to obtain a reliable operation of the actuating means.

BRIEF DESCRIPTION OF THE DRAWINGS

Other advantages and characteristics of the invention will be clear from the following description, reference being made to the attached drawings.

In the drawings:

FIG. 9 is an unrolled view of a part of a seventh embodiment of the intermediate member according to the invention.

FIG. 10 is an unrolled view of a part of an eighth embodiment of the intermediate member according to the invention in a pre-assembled condition.

FIG. 11 is a cross-section view of the unit with an intermediate member according to FIG. 11 in the pre-assembled condition.

FIG. 12 is an unrolled view of a part of the eighth embodiment of the intermediate member according to the invention in the assembled condition.

FIG. 13 is a cross-section view of the instrument with an intermediate member according to FIG. 10 in the assembled condition.

F*ig*.17 is a schematic exploded view of a modified embodiment of the instrument according to the invention.

Figure 18:
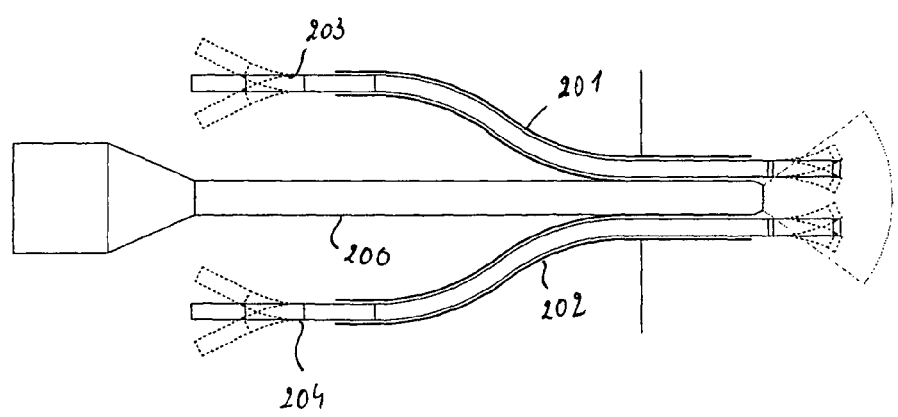

FIG. 18 is a schematic drawing of a special application of a modified instrument according to the invention.

Figure 1:
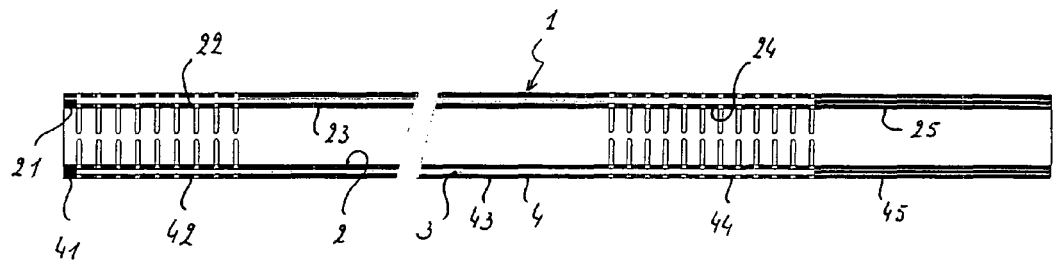
FIG. 1 is a schematic cross-section of an instrument according to the invention.
Figure 2:
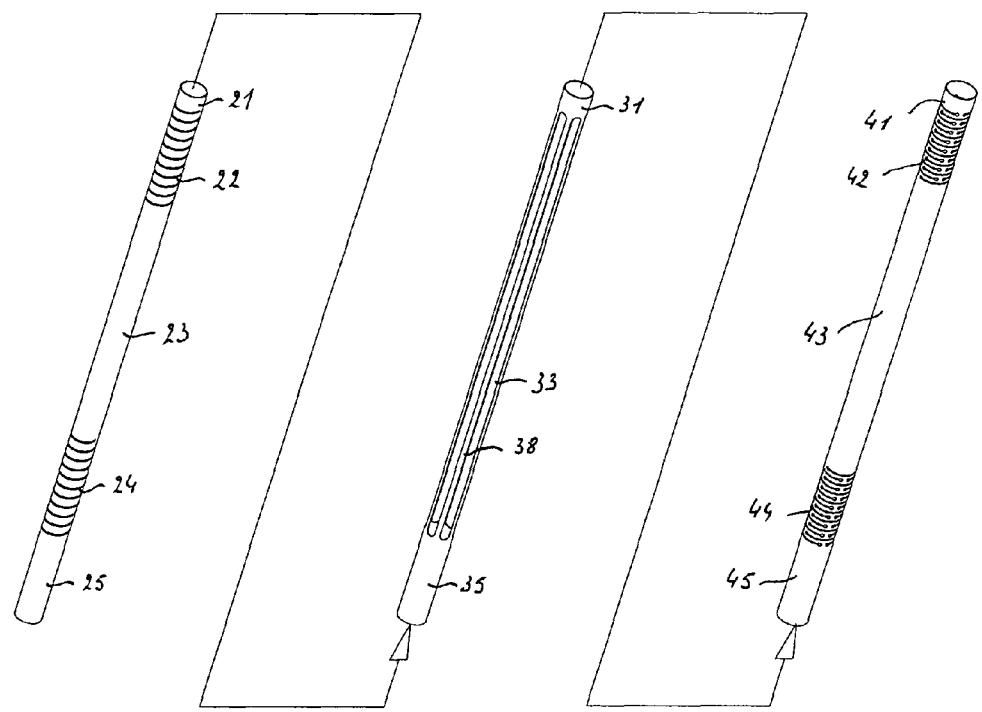
FIG. 2 is an exploded view of the three cylindrical members forming the instrument according to the invention.
Figure 19:
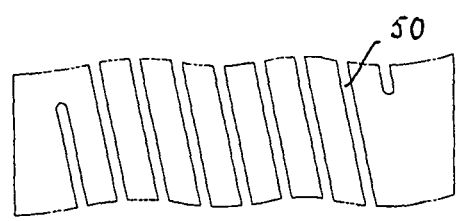

FIG. 19 is a schematic presentation of an unrolled view of a first embodiment of a flexible part of a cylindrical member as shown in FIG. 1 or 2.

Figure 20:
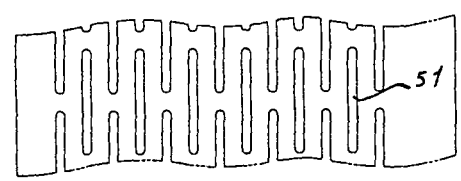

FIG. 20 is an unrolled view of a second embodiment of a flexible part of a cylindrical member as shown in FIG. 1 or 2.

Figure 21:
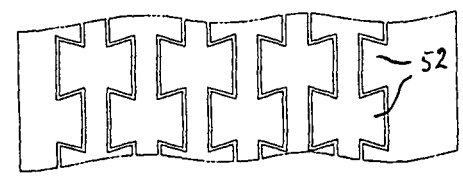

FIG. 21 is an unrolled view of a third embodiment of a flexible part of a cylindrical member as shown in FIG. 1 or 2.

Figure 14:
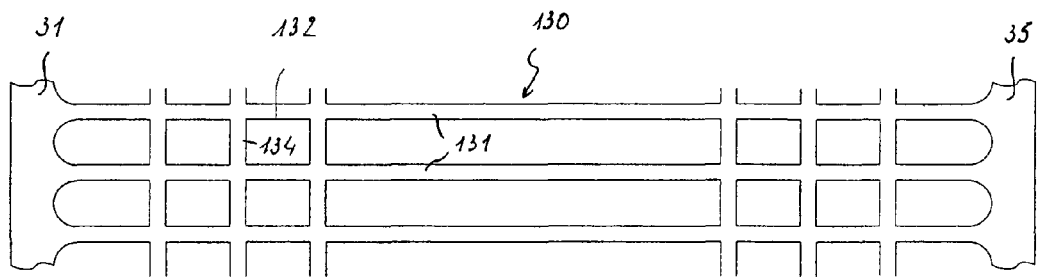
FIG. 14 is an unrolled view of a part of a ninth embodiment of the intermediate member according to the invention in a pre-assembled condition.
Figure 15:
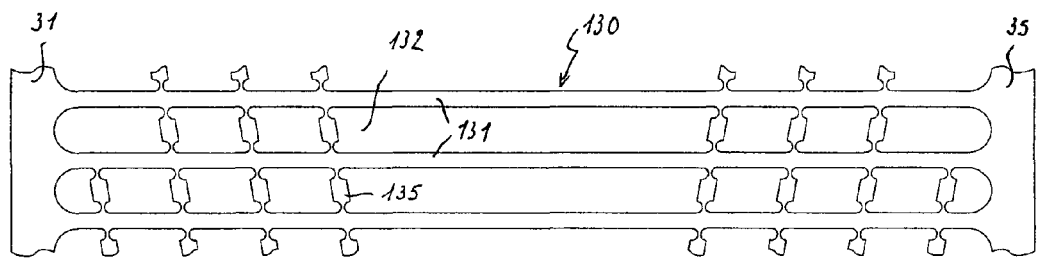
FIG. 15 is an unrolled view of a part of a tenth embodiment of the intermediate member according to the invention.
Figure 16:
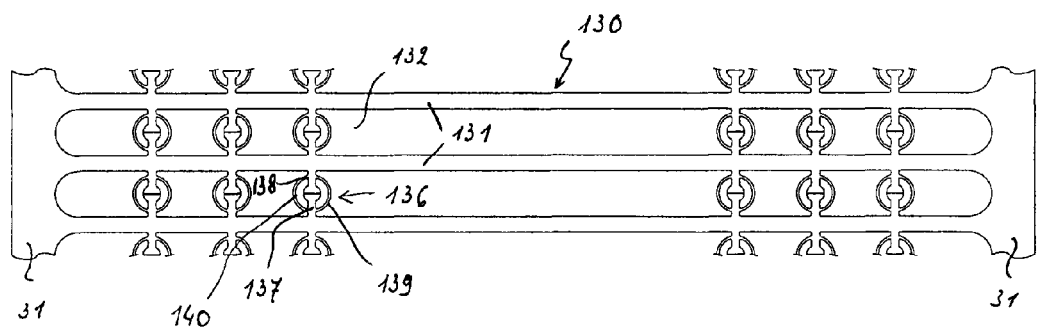
FIG. 16 is an unrolled view of a part of an eleventh embodiment of the intermediate member according to the invention.
Figure 22:
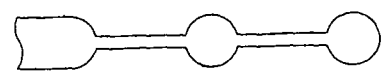

FIG. 22 is a view of a flexible part as a guiding member between two longitudinal elements as shown in FIGS. 14-16.

Figure 23:
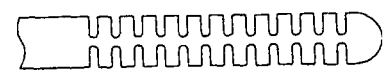

FIG. 23 is a view of an embodiment of a flexible part as a guiding member as modified with respect to FIG. 22.

DETAILED DESCRIPTION OF THE INVENTION

In FIG. 1 there is shown an axial cross-section of an instrument 1 according to the invention. The instrument 1 is composed of three coaxial cylindrical members: an inner member 2, an intermediate member 3 and an outer member 4. The inner cylindrical member 2 is composed of a first rigid end part 21, which is the part normally used at the location which is difficult to reach or inside the human body, a first flexible part 22, an intermediate rigid part 23, a second flexible part 24 and a second rigid end part 25 which is normally used as the operating part of the instrument in that it serves to steer the other end of the unit. The outer cylindrical member 4 is in the same way composed of a first rigid part 41, a flexible part 42, an intermediate rigid part 43, a second flexible part 44 and a second rigid part 45. The length of the different parts of the cylindrical members 2 and 4 are substantially the same so that when the cylindrical member 2 is inserted into the cylindrical member 4, the different parts are positioned against each other. The intermediate cylindrical member 3 also has a first rigid end part 31 and a second rigid end part 35 which in the assembled condition are located between the corresponding rigid parts 21, 41 and 25, 45 respectively of the two other cylindrical members.

From FIG. 2 it will be clear to a person skilled in the art that a radial deflection of the handling end portion of the instrument 1 can be caused by a radial deflection of the actuating end portion of the instrument through a movement of the longitudinal elements 38 in a longitudinal direction. FIG. 18 further illustrates this by the radial deflections of the handling end portions of the instruments 203 and 204 in response to the radial deflections of the actuating end portions of these instruments.

The intermediate part 33 of the intermediate cylindrical member 3 is formed by three or more separate longitudinal elements which can have different forms and shapes as will be explained below. After assembly of the three cylindrical members 2, 3 and 4 whereby the inner member 2 is inserted in the intermediate member 3 and the two combined members 2, 3 are inserted into the outer member 4, the end faces of the three members 2, 3 and 4 are connected to each other at both ends so as to have one integral unit.

Figure 3:
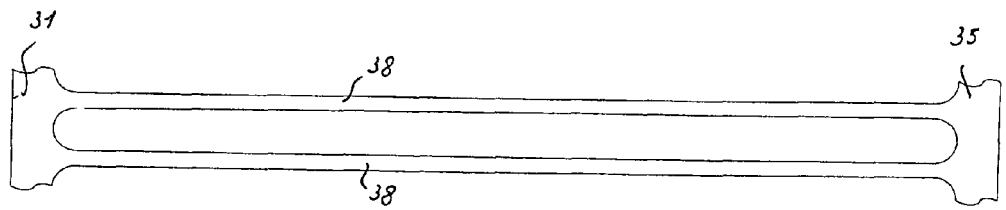
FIG. 3 is an unrolled view of a part of the intermediate cylindrical member of the instrument according to the invention.

In the embodiment shown in FIG. 2 the intermediate part 33 is formed by a number of longitudinal elements 38 with a uniform cross-section so that the intermediate part 33 has the general shape and form as shown in the unrolled condition in FIG. 3. From this it also becomes clear that the intermediate part is formed by a number of equally spaced parallel longitudinal elements 38 over the circumference of the cylindrical part 3. The number of elements 38 must be at least three, so that the instrument 1 becomes fully controllable in any direction, but any higher number is possible as well.

The production of such an intermediate part is most conveniently done by injection molding or plating techniques or starting from a regular cylindrical tube with desired inner and outer diameters and removing these parts of the tube wall required to end up with the desired shape of the intermediate cylindrical member. This removal of material can be done by means of different techniques such as laser cutting, photo-chemical etching, deep pressing, conventional chipping techniques such as drilling or milling, high pressure water jet cutting systems or any suitable material removing process available. Preferably laser cutting is used as this allows a very accurate and clean removal of material under reasonable economic conditions. These are convenient ways the intermediate member 3 can be made in one process, without requiring additional steps for connecting the different parts of the intermediate cylindrical member as required in the conventional instruments, where the longitudinal members must be connected in some way to the end parts.

The same type of technology can be used for producing the inner and outer cylindrical members 2 and 4 with their respective flexible parts 22, 24, 42 and 44. A tube having flexible parts can be obtained in different ways. In FIGS. 19, 20, 21 and 22 there are shown different ways how such flexibility in the part can be obtained. FIG. 19 shows a schematic representation of a rolled out flexible cylindrical portion. In the embodiment shown in FIG. 19, the part of the cylindrical tube to become flexible has been provided with slits 50 extending in a helical manner over the length of the flexible part. The flexibility can be controlled by the number of slits 50 and/or the angle of the slits 50 with respect to the axial direction of the cylindrical member.

In the embodiment of FIG. 20, the part of the cylindrical tube to become flexible has been provided with a number of short slits 51. The slits 51 can be divided into groups, the slits 51 in each group being located in the same line extending perpendicular to the axis of the cylindrical member. The slits 51 in two neighboring groups are offset. In the embodiment of FIG. 21, the part of the cylindrical tube to become flexible has been provided by making slits producing a number of swallow's tails 52 which fit into each other as shown.

It will become obvious that other systems of providing a flexible part in a cylindrical tube wall may be used as well. More specifically, it is possible to use combinations of the systems described above. Otherwise, it will also become obvious that the advantageous process for producing such flexible parts in a cylindrical tube as described above may be used in the production of the intermediate part 33.

As described above in the first embodiment, the longitudinal elements 38 are formed by a number of parallel elements equally spaced around the circumference of the cylindrical member 3. As shown in FIG. 3, a free space is available between each pair of adjacent elements 38. It is possible to use longitudinal elements 38 as shown in this figure, but in the flexible parts of the instrument there will be a tendency of the longitudinal elements 38 to move in a tangential direction especially when strong curves have to be made. As a consequence of this uncontrolled movement of the longitudinal elements 38, the accuracy and the magnitude of the control of the position of the one end portion by the movement of the other end portion may be lost or become more complicated. This problem can be avoided by making longitudinal elements 38 in such a way that the free space between two adjacent elements 38 is as small as possible or completely left out so that two adjacent longitudinal elements 38 are touching each other and serve as a guide for each other. A disadvantage of this system however is that a large number of longitudinal elements 38 must be present, as the cross section of these elements must be chosen in such a way that their flexibility in any direction is almost the same independent of the direction of bending. As the wall thickness of the cylindrical member is relatively small compared to the overall dimensions of the cylindrical member especially with respect to the circumference, this will result in a large number of longitudinal elements 38 as seen along the tangential direction and an increase of total bending stiffness. As the longitudinal elements 38 are touching each other in the tangential direction, this provides for a guiding of these elements upon use of the instrument.

In a modified embodiment of the longitudinal elements this problem has been avoided in a different way. In this second embodiment shown in FIG. 4 each longitudinal element 60 is composed of three portions 61, 62 and 63, co-existing with the first flexible portion 22, 42, the intermediate rigid portion 23, 43 and the second flexible portion 24, 44 respectively. In the portion 62 coinciding with the intermediate rigid portion, each pair of adjacent longitudinal elements 60 is touching each other in the tangential direction so that in fact only a narrow gap is present therebetween just sufficient to allow independent movement of each longitudinal element.

In the other two portions 61 and 63 each longitudinal element consists of a relatively small and flexible strip 64, 65 as seen in circumferential direction, so that there is a substantial gap between each pair of adjacent strips, and each strip 64, 65 is provided with a number of cams 66, extending in circumferential direction and almost completely bridging the gap to the next strip. Because of these cams the tendency of the longitudinal elements in the flexible portions of the instrument to shift in circumferential direction is suppressed and the direction control is complete. The exact shape of these cams 66 is not very critical, provided they do not compromise flexibility of strips 64 and 65. In view thereof, any shape like a trapezium shape as shown in FIG. 4 is applicable.

Figure 4:
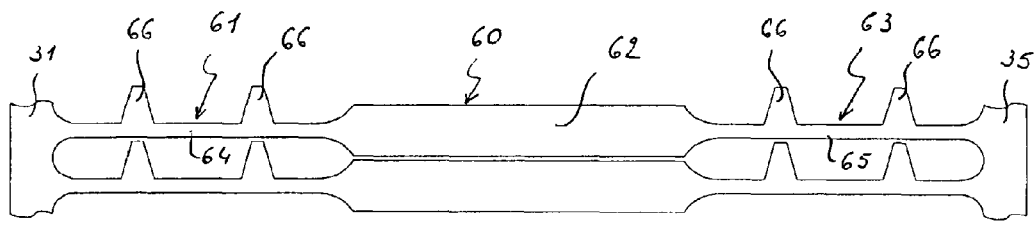
FIG. 4 is an unrolled view of a part of a second embodiment of the intermediate member according to the invention.

In the embodiment shown in FIG. 4, the cams 66 are extending towards one direction as seen from the strip to which they are connected. It is however also possible to have these cams extending to both circumferential directions starting from one strip. By using this it is either possible to have an alternating type of strips as seen along the circumference, a first type provided at both sides with cams 66 extending until the next strip, or a second intermediate set of strips without cams. Otherwise it is possible to have strips with cams at both sides, where as seen along the longitudinal direction of the instrument the cams originating from one strip are alternating with cams originating from the adjacent strips. It is obvious that numerous alternatives are available. It is important that adjacent strips are in contact with each but that the flexibility of strips 64 and 65 is not compromised.

Figure 5:
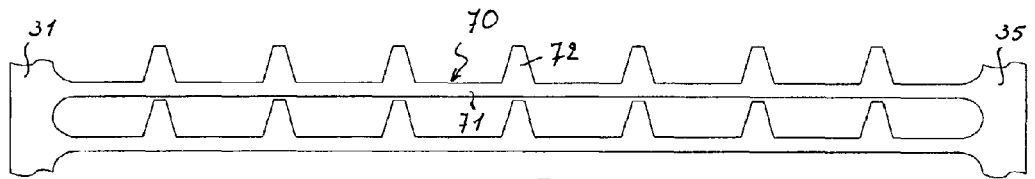
FIG. 5 is an unrolled view of a part of a third embodiment of the intermediate member according to the invention.

In FIG. 5 there is shown a third embodiment of the longitudinal elements as may be used according to the invention. In this embodiment, the longitudinal elements 70 are formed by strips 71 comparable to the strips 38 of FIG. 3 interconnecting the portions 31 and 33. Furthermore, the strips 71 have been provided with cams 72 so that the strips 71 are almost comparable to the strips 61 or 63 of FIG. 4. In this way a guiding is provided by the cams 72 over the complete length of the strips 71. It is obvious that in this case the modifications with respect to the position of the cams 72 and the alternating of strips 71 with cams on both sides and strips without cams as described above with respect to FIG. 4 are also applicable for this embodiment.

Figure 6:
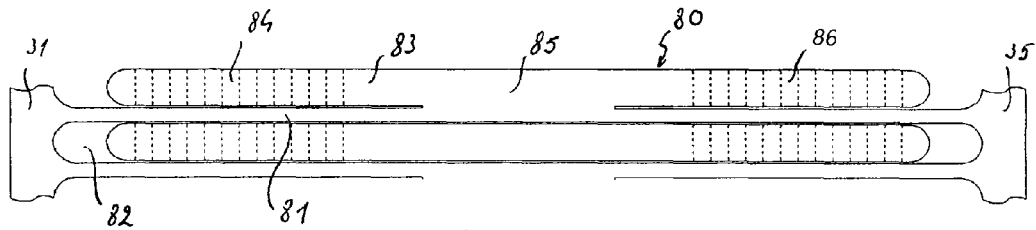
FIG. 6 is an unrolled view of a part of a fourth embodiment of the intermediate member according to the invention.

In the fourth embodiment shown in FIG. 6, the longitudinal elements 80 are formed by strips 81 interconnecting the portions 31 and 35. These strips are comparable to the strips 38 in FIG. 3 and have substantially the same width. This means that between each pair of adjacent strips 81 there is left a circumferential gap 82. Each gap 82 is filled substantially by means of another strip 83, having a circumferential width slightly smaller than the circumferential width of the gap 82 and a longitudinal dimension which leaves some play between the ends of the axial ends of the strip 83 and the portions 31 and 35 respectively. The strip 85 is composed of three parts, a first flexible part 84, schematically represented with dotted lines, an intermediate part 85 and a second flexible part 86, the three parts coinciding with the flexible parts 22, 42, the intermediate parts 23, 43 and the flexible parts 24, 44 respectively of the instrument. The flexibility of the parts 84 and 86 may be obtained by any system described above, or as shown in FIGS. 22 and 23. The intermediate part 85 is connected to the strip 81. In this way the strip 85 is guiding the movement of the strips 81 in the flexible portions of the instrument, without hindering their longitudinal movement.

In the embodiment shown, each strip 81 is on one side connected to a strip 83. As an alternative it is also possible to have a system in which as seen along the circumference of the intermediate cylindrical member this member is composed of a first set of strips 81 having both sides connected to a strip 83, and a second set of strips 81 which have no connection to such strips 83 and are as such comparable to the strips 38 of FIG. 3. It is of course obvious that other solutions are available by using combinations of strips 81 having either no, one or two connections to strips 83 by putting them in the right sequence along the circumference of the intermediate cylindrical member.

Figure 7:
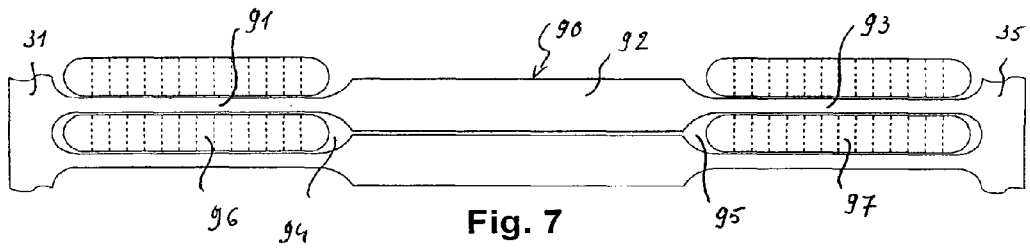
FIG. 7 is an unrolled view of a part of a fifth embodiment of the intermediate member according to the invention.

A fifth embodiment has been shown in FIG. 7. In this embodiment, each longitudinal element 90 is composed of a first strip 91, a band 92 and a second strip 93. The first and second strips 91 and 93 each have a circumferential width such that there is a circumferential gap 94 and 95 respectively between each pair of adjacent strips 91 and 93 respectively.

The bands 92 have a circumferential width such that two adjacent bands are in contact with each other. The strips 91 and 93 coincide with the flexible portions 22, 42 and 24 and 44 respectively whereas the bands 92 coincide with the intermediate portion 23, 43. In each gap 94 and 95 respectively, plates 96 and 97 are placed which plates 96, 97 have a circumferential width filling the width of the gap 94, 95 and thus providing a guiding for the strips 91 and 93 respectively. Free movement of the strips is achieved in that in the longitudinal direction there is some play between the axial ends of the plates 96, 97 and the portion 31, the bands 92 and the portion 35 respectively.

The plates 96, 97 are completely free to move in their respective gaps 94, 95 respectively, but because of the selected dimensions only a movement in longitudinal direction is available. For the production of such a system as shown in FIG. 7 it is possible to first make the intermediate cylindrical elements by means of one of the production techniques described above, which results in an intermediate cylindrical member which is different from the one shown in FIG. 7 in that one point of each plate 96 and 97 is still connected either to an adjacent strip, to a band, or to the portions 31 or 35. In this form, the instrument is assembled whereby the connection point between the plates 96 or 97 and the remainder of the intermediate cylindrical member coincides with a hole provided in the cylindrical member 4. Once the assembling is finished, the connection mentioned above can be destroyed, for example by using one of the production techniques mentioned above. In this way, the plates 96, 97 become completely freely movable in their gaps. Here once more it will become obvious that the laser technology is very effective in this production step.

Figure 8:
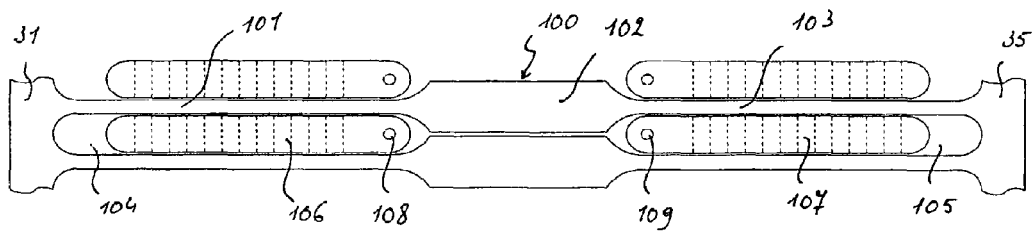
FIG. 8 is an unrolled view of a part of a sixth embodiment of the intermediate member according to the invention.

In FIG. 8, there is shown a sixth embodiment of the intermediate cylindrical member according to the invention. This embodiment is very similar to the embodiment shown in FIG. 7, in that the longitudinal elements 100 are composed of strips 101 and 103 comparable to the strips 91 and 93, and a band 102 comparable to the band 92. In the same way, the gaps 104 and 105 are comparable to the gaps 94 and 95, and are occupied by plates 106 and 107, which are comparable to the plates 96 and 97. In this embodiment, the plates 106 and 107 are not completely free from the remainder of the instrument, but each plate 106 and 107 is connected either to the outer cylindrical member 4 or to the inner cylindrical member 2, especially in the non-flexible part thereof. In the embodiment shown, this is achieved by welding at one point, 108 and 109 respectively, the plates 106 and 107 to the intermediate rigid portion of either the inner or outer cylindrical member 2 or 4. In this way, the strips 101 and 103 are accurately guided by the plates 106 and 107 in the flexible portions of the instrument, but the plates 106 and 107 are not free to move whereby the control of movement is improved and the assembling of the instrument becomes much easier.

The seventh embodiment, shown in FIG. 9 can be seen as a combination of the embodiment of FIG. 6 and the embodiment of FIG. 8. The longitudinal element 110 consists of a number of strips 111, comparable to the strips 81 and the gap 112 between each pair of adjacent strips 111 is occupied by a strip or plate 113 comparable to strip 83. In this embodiment the strips 113 are not connected to the strips 111 as in the embodiment of FIG. 6, but are connected at some points 115, 116 to the rigid intermediate part of either the outer or inner cylindrical member 2 or 4 of the instrument comparable to the embodiment of FIG. 8.

In FIGS. 10, 11, 12 and 13 there is shown an embodiment of the instrument which can be seen as a modification of the embodiment shown in FIG. 9. In FIGS. 10 and 11 there is shown a situation before assembly whereas FIGS. 12 and 13 show the assembled instrument.

In FIGS. 10 and 11 there is shown the outer cylindrical element 4, which is composed of three parts, a part 121 forming the first flexible portion 42 and the first rigid portion 41, a part 122 forming the intermediate rigid portion 43 and also forming the guiding plates 124 comparable to the guiding plates 106, 107 in FIG. 8 and a part 123 forming the second flexible part 44 and the second rigid part 45.

The parts 121 and 123 are simple cylindrical tubes which have been provided with a flexible portion by one of the methods described above. The intermediate portion 122 is formed by a cylindrical tube in which, by one of the processes described above for removal of material, a number of tongues 124 have been made flexible by one of the methods described above. These tongues extend from both ends of a central portion and form bands which occupy the space between strips like the strips 111. Therefore the tongues are deformed at their connection with the central portion 125 so as to have a smaller diameter whereby these tongues fit into the spaces between the strips. In fact the tongues are deformed to form internal and external diameters substantially equal to the corresponding diameters of the strips.

After the different parts 121, 122 and 123 are produced as described, the parts 121 and 123 are moved over the tongues 124 and the respective abutting ends of the parts 121 and 123 are welded to the central portion 125 so as to form the external cylindrical member 4.

In FIGS. 14, 15 and 16 there is shown a different category of embodiments of longitudinal elements 130 interconnecting the portions 31 and 35 of the intermediate cylindrical member 3. The longitudinal elements 130 are formed by strips 131 comparable to the strips 38 of FIG. 3. As seen in the circumferential direction of the cylindrical member, these strips are spaced apart from each other by a gap 132. At least in the flexible zone of the instrument where a guiding of the strips is preferred or required, each pair of adjacent strips is connected by a number of bridges which have a defined degree of flexibility as seen in the longitudinal direction. These bridges extend the width of the gap 132 and can be shaped in different ways.

In the embodiment of FIG. 14, the bridges have the form of short strips 134 extending in the circumferential direction and having a width in the longitudinal direction which allows some parallel movement from one strip 131 to an adjacent strip 131. By selection of the number of short strips 134 and the cross-sectional dimensions thereof, the flexibility of the short strips 134 may be sufficient to allow sufficient freedom of movement of the adjacent strips 131. If needed, the flexibility of the short strips 134 can be enhanced by applying some special configurations as shown in FIGS. 23, 24 and 25. The short strips 134 need not transfer any tangential force from one strip 131 to the adjacent strip 131, but serve only to maintain the distance between two adjacent strips 131.

In the embodiment shown in FIG. 15, the strips 135 are shaped with some recesses so as to increase their flexibility. Moreover these strips 135 have been not directed along the circumferential direction of the cylindrical member, but are positioned under a small angle with respect to the circumferential direction in a way that the series of connectors form a spiral. A special shape of the bridges is shown in the embodiment of FIG. 16. The bridges 136 of this embodiment consist of two cams 137 and 138 extending from two adjacent strips 131 and abutting about halfway in the gap between the two strips. Two semicircular bands 139 and 140 connect the two cams 137 and 138. This provides a high degree of flexibility while the distance between the two adjacent strips is accurately maintained. The making of such bridges 136 does not present any special problems when using one of the techniques described above.

Figure 17:
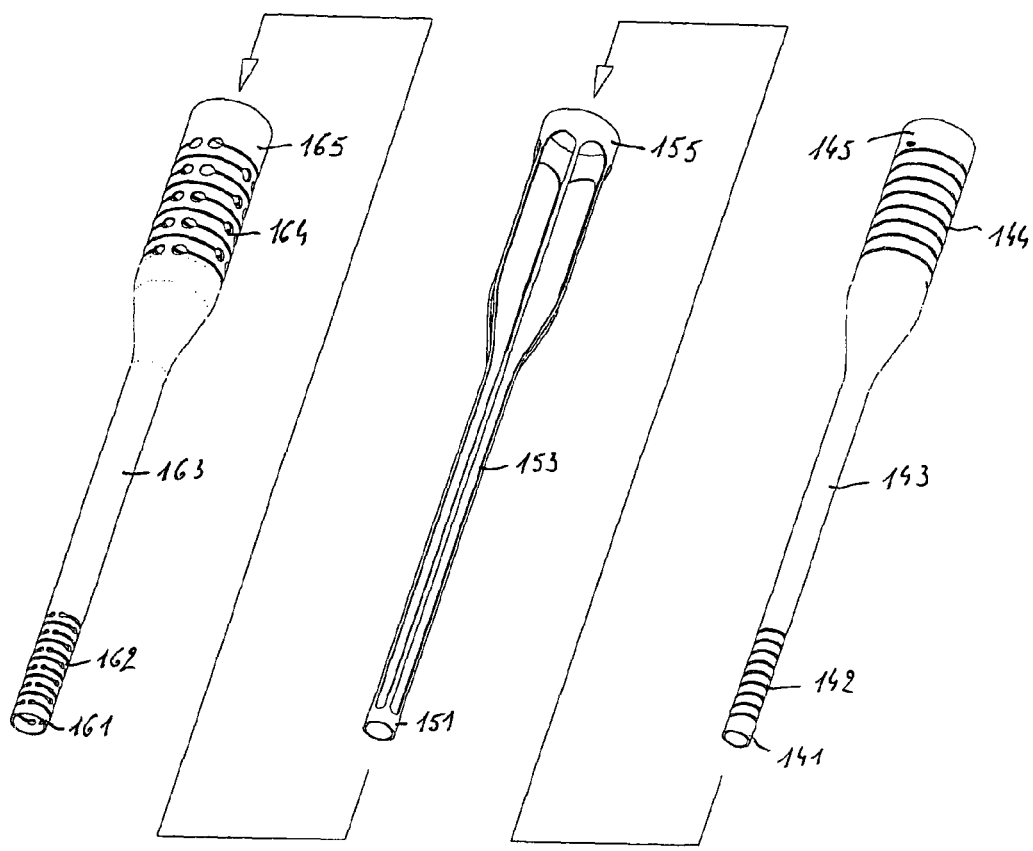

In FIG. 17, there is shown a special embodiment of an instrument according to the inventions. The inner cylindrical member is composed of a first rigid end part 141, a first flexible part 142, an intermediate rigid part 143, a second flexible part 144 and a second rigid end part 145 which is normally used as the operating part of the instrument in that it serves to steer the other end of the unit. The outer cylindrical member is in the same way composed of a first rigid part 161, a flexible part 162, an intermediate rigid part 163, a second flexible part 164 and a second rigid part 165. The intermediate cylindrical member also has a first rigid end part 151 and a second rigid end part 155 which in the assembled condition are located between the corresponding rigid parts 141, 161 and 145, 165 respectively of the two other cylindrical members. In the embodiment shown the longitudinal elements 153 are of the type shown in FIG. 3, but it will become obvious that any other type described above may be used as well. So far the construction is comparable to the instrument shown in FIG. 1.

The main difference with respect to the embodiment of FIG. 1 consists in the use of a different set of diameters for some parts of the instrument. In the embodiment shown, the parts 144, 145, 155, 164 and 165 have a larger diameter than the other parts and in the parts 143, 153 and 163 a frusto-conical portion is formed in order to connect the smaller diameter parts with the larger diameter parts. As shown in FIG. 17, the different parts can easily be assembled by inserting one into the other. The main reason however to have such an instrument with different diameters is that by using an operating part with a larger diameter, the movement of the other end is amplified, whereas if a smaller diameter is used the movement of the other end is reduced. Depending on the application and its requirements, larger diameters can be used to provide the amplified movement or smaller diameters can be used to reduce the movement and increase accuracy.

A special application of the instrument according to the invention is shown in FIG. 18. In this application, a number of tubes have been inserted into a body of an environment where some inspection or treatment must take place. In the embodiment shown there are three tubes including a first or central tube 200, which may be a straight tube which is used for illumination and viewing purposes. Two S-shaped tubes 201 and 202 are positioned partly against this central tube 200, and these tubes are used for the guiding of instruments 203 and 204 according to the invention. The bending is necessary to have the handling side of the instruments 203 and 204 removed from each other and from the central tube 200 so that the movement is possible in any direction. By positioning the S-shaped tubes diametrically in opposition to the central tube 200, there is also sufficient space left at the working side to perform all kinds of movement of these ends of the instruments 203 and 204.

In order to enable the instruments to be guided through such an S-shaped tube 201 or 202 or a tube with any curved shape, the intermediate rigid portion of the instruments 203 and 204 is provided with at least one additional flexible portion dividing the intermediate portion in rigid portions of a lesser length so as to allow some additional bending. If needed, more than one intermediate flexible portion may be included.

It is obvious that the invention is not restricted to the described embodiments as shown in the attached drawings, but that within the scope of the claims modifications can be applied without departing from the inventive concept.

The invention claimed is:

1. A process of producing an instrument for endoscopic applications, the instrument comprising a tubular member that includes three coaxial cylindrical members, the process including:
   providing an inner cylindrical member including a first rigid inner member end part connected to a handling end portion of the instrument, a first flexible inner member part, an intermediate rigid inner member part, a second flexible inner member part, and a second rigid inner member end part connected to an actuating end portion of the instrument;
   providing a full cylindrical tube, and making a number of longitudinal slits in the cylindrical tube so as to form separate longitudinal elements in the cylindrical tube and to produce an intermediate cylindrical member including a first rigid intermediate member end part at the handling end portion of the instrument, and a second rigid intermediate member end part at the actuating end portion of the instrument that is connected to the first rigid intermediate member end part via three or more of the separate longitudinal elements, each of the longitudinal elements being connected to both the first rigid intermediate member end part and the second rigid intermediate member end part;
   providing an outer cylindrical member including a first rigid outer member end part at the handling end portion of the instrument, a first flexible outer member part, an intermediate rigid outer member part, a second flexible outer member part, and a second rigid outer member end part at the actuating end portion of the instrument;
   inserting the inner cylindrical member into the intermediate cylindrical member and inserting the intermediate cylindrical member into the outer cylindrical member;
   connecting the first rigid inner member end part, the first rigid intermediate member end part and the first rigid outer member end part to each other; and
   connecting the second rigid inner member end part, the second rigid intermediate member end part and the second rigid outer member end part to each other such that the longitudinal elements of the intermediate cylindrical member are arranged to control a radial deflection of the handling end portion of the instrument by a radial deflection of the actuating end portion of the instrument through a movement of the longitudinal elements in a longitudinal direction.

2. The process according to claim 1, further including forming the longitudinal slits by a material removal technique.

3. The process according to claim 2, wherein the material removal technique is at least one of photochemical etching, deep pressing, chipping techniques, and laser cutting.

4. The process according to claim 1, further including connecting the first rigid inner member end part, the first rigid intermediate member end part and the first rigid outer member end part to each other, and connecting the second rigid inner member end part, the second rigid intermediate member end part and the second rigid outer member end part to each other so as to form one integral unit.

5. The process according to claim 1, further including forming the inner cylindrical member by at least one of photochemical etching, deep pressing, chipping techniques, and laser cutting.

6. The process according to claim 1, further including forming the outer cylindrical member by at least one of photochemical etching, deep pressing, chipping techniques, and laser cutting.

7. An instrument for endoscopic applications, comprising a tubular member that includes three coaxial cylindrical members, including an inner cylindrical member, an intermediate cylindrical member, and an outer cylindrical member;
   the inner cylindrical member including a first rigid inner member end part connected to a handling end portion of the instrument, a first flexible inner member part, an intermediate rigid inner member part, a second flexible inner member part, and a second rigid inner member end part connected to an actuating end portion of the instrument;
   the intermediate cylindrical member including a first rigid intermediate member end part at the handling end portion of the instrument, and a second rigid intermediate member end part at the actuating end portion of the instrument that is connected to the first rigid intermediate member end part via three or more separate longitudinal elements, each of the longitudinal elements being connected to both the first rigid intermediate member end part and the second rigid intermediate member end part; and
   the outer cylindrical member including a first rigid outer member end part at the handling end portion of the instrument, a first flexible outer member part, an intermediate rigid outer member part, a second flexible outer member part, and a second rigid outer member end part at the actuating end portion of the instrument;
   the first rigid inner member end part, the first rigid intermediate member end part and the first rigid outer member end part being connected to each other, and the second rigid inner member end part, the second rigid intermediate member end part and the second rigid outer member end part being connected to each other such that the longitudinal elements of the intermediate cylindrical member are arranged to control a radial deflection of the handling end portion of the instrument by a radial deflection of the actuating end portion of the instrument through a movement of the longitudinal elements in a longitudinal direction.

8. The instrument according to claim 7, wherein the intermediate member is a cylindrical tube having at least three longitudinal slits forming the longitudinal elements, each longitudinal slit starting at the first rigid intermediate member end part and ending at the second rigid intermediate member end part, and at least one longitudinal element of the at least three longitudinal elements including at least one protrusion extending in a radial direction towards an adjacent one of the at least three longitudinal elements.

9. The instrument according to claim 8, wherein the protrusions are only present in parts of the at least one longitudinal element coinciding with a first location between the first flexible inner member part and the first flexible outer member part, and a second location between the second flexible inner part and the second flexible outer member part.

10. The instrument according to claim 9, wherein in at least part of a non-flexible portion of the tubular member, the longitudinal elements have a circumferential width so as to substantially fill up the width of the longitudinal slits.

11. The instrument according to claim 7, wherein the intermediate cylindrical member is a cylindrical tube having at least three longitudinal slits forming the longitudinal elements, each longitudinal slit starting at the first rigid intermediate member end part and ending at the second rigid intermediate member end part, and adjacent longitudinal elements are interconnected by at least one flexible bridge, at least in parts of the adjacent longitudinal elements coinciding with a first location between the first flexible inner member part and the first flexible outer member part, and a second location between the second flexible inner member part and the second flexible outer member part.

12. The instrument according to claim 7, wherein each of the longitudinal elements is disposed:
in a first zone adjacent to the handling end portion in a cylindrical section with a first diameter;
in a second zone adjacent to the actuating end portion in a cylindrical section with a second diameter that is different than the first diameter; and
in an intermediate zone in a conical section interconnecting the first and second zones.

13. The instrument according to claim 12, wherein the first diameter is smaller than the second diameter.

14. The instrument according to claim 7, wherein the intermediate cylindrical member is a cylindrical tube
having at least three longitudinal slits forming the longitudinal elements, each longitudinal slit starting at the first rigid intermediate member end part and ending at the second rigid intermediate member end part, the longitudinal slits being formed by material removal technique, and each longitudinal slit between adjacent longitudinal elements having such a width that the adjacent longitudinal elements are parallel to each other upon actuation of the instrument.

15. The instrument according to claim 14, wherein the material removal technique is at least one of photochemical etching, deep pressing, chipping techniques, and laser cutting.

16. The instrument according to claim 7, wherein the intermediate cylindrical member is a cylindrical tube having at least three longitudinal slits forming the longitudinal elements, each longitudinal slit starting at the first rigid intermediate member end part and ending at the second rigid intermediate end part, the longitudinal slits being formed by a material removal technique, and at least one longitudinal slit of the number of longitudinal slits between a pair of adjacent longitudinal elements being provided with at least one element configured to maintain the pair of adjacent longitudinal elements parallel to each other.

17. The instrument according to claim 16, wherein the material removal technique is at least one of photochemical etching, deep pressing, chipping techniques, and laser cutting.

18. The instrument according to claim 7, wherein the first rigid inner member end part, the first rigid intermediate member end part and the first rigid outer member end part are connected to each other, and the second rigid inner member end part, the second rigid intermediate member end part and the second rigid outer member end part are connected to each other so as to form one integral unit.

19. The instrument according to claim 7, wherein the intermediate cylindrical member is a cylindrical tube having at least three longitudinal slits forming the longitudinal elements, each longitudinal slit starting at the first rigid intermediate member end part and ending at the second rigid intermediate member end part, and each longitudinal slit between adjacent longitudinal elements having such a width that the adjacent longitudinal elements are parallel to each other upon actuation of the instrument.

20. The instrument according to claim 7, wherein the intermediate cylindrical member is a cylindrical tube having at least three longitudinal slits forming the longitudinal elements, each longitudinal slit starting at the first rigid intermediate member end part and ending at the second rigid intermediate member end part, and at least one longitudinal slit between a pair of adjacent longitudinal elements being provided with at least one element configured to maintain the longitudinal elements parallel to each other.

21. The instrument according to claim 20, wherein each longitudinal slit is filled with a strip having flexible portions coinciding with a first location between the first flexible inner member part and the first flexible outer member, and a second location between the second flexible inner member and the second flexible outer member part.

22. The instrument according to claim 21, wherein each strip has a central part coinciding with a non-flexible portion of the tubular member, and is connected to an adjacent one of the longitudinal elements.

23. The instrument according to claim 20, wherein in at least part of a non-flexible portion of the tubular member, the longitudinal elements have a circumferential width so as to substantially fill up the width of the longitudinal slits, and each of the remaining parts of the longitudinal slits are filled up with a strip.

24. The instrument according to claim 23, wherein each of the strips have one end connected to a part of the intermediate rigid inner member part at the actuating end portion of the instrument.

25. The instrument according to claim 23, wherein each of the strips have one end connected to a part of the intermediate rigid inner member part at the handling end portion of the instrument.

26. The instrument according to claim 23, wherein each of the strips have one end connected to a part of the intermediate rigid outer member part at the handling end portion of the instrument.

27. The instrument according to claim 23, wherein each of the strips have one end connected to a part of the intermediate rigid outer member part at the actuating end portion of the instrument.

28. The instrument according to claim 7, wherein the intermediate cylindrical member is a cylindrical tube having at least three longitudinal slits forming the longitudinal elements, each longitudinal slit starting at the first rigid intermediate member end part and ending at the second rigid intermediate member end part, the longitudinal slits being formed by a material removal technique, and at least one longitudinal element of the three or more longitudinal elements including at least one protrusion extending in a radial direction towards an adjacent longitudinal element.

29. The process according to claim 28, further including forming the outer cylindrical member by at least one of photochemical etching, deep pressing, chipping techniques, and laser cutting.

30. The instrument according to claim 7, wherein at least the intermediate cylindrical member is formed by at least one of injection molding and plating so as to form the first rigid intermediate member end part, the second rigid intermediate member end part, and the three or more separate longitudinal elements, the longitudinal elements being separated from each other by at least three longitudinal slits that have such a width that the longitudinal elements are parallel to each other upon actuation of the instrument.

31. The instrument according to claim 7, wherein at least the intermediate cylindrical member is formed by at least one of injection molding and plating so as to form the first rigid intermediate member end part, the second rigid intermediate member end part, and the three or more separate longitudinal elements, wherein the longitudinal elements are separated from each other by at least three longitudinal slits, and wherein at least one longitudinal slit between a pair of adjacent longitudinal elements includes elements so as to maintain the pair of adjacent longitudinal elements parallel to each other.

32. The instrument according to claim 7, wherein at least the intermediate cylindrical member is formed by at least one of injection molding and plating so as to form the first rigid intermediate member end part, the second rigid intermediate member end part, and the three or more separate longitudinal elements, at least one longitudinal element including at least one protrusion extending in a radial direction towards an adjacent longitudinal element.

\* \* \* \* \*